United States Patent [19]

Sandler et al.

[11] Patent Number: 5,436,373
[45] Date of Patent: Jul. 25, 1995

[54] PROCESS FOR THE PREPARATION OF N-BENZYL-N-ORGANOAMINOALKANOL

[75] Inventors: Stanley R. Sandler, Springfield; Doris L. Baer, Pottstown, both of Pa.

[73] Assignee: Elf Atochem North America, Inc., Philadelphia, Pa.

[21] Appl. No.: 329,594

[22] Filed: Oct. 26, 1994

[51] Int. Cl.$^6$ .................. C07C 213/00; C07C 213/02
[52] U.S. Cl. ....................... 564/386; 560/42; 558/422
[58] Field of Search ............. 564/386, 391, 384; 560/42; 558/422

[56] References Cited

U.S. PATENT DOCUMENTS

| | | | |
|---|---|---|---|
| 2,828,320 | 3/1958 | Freifelder | 260/472 |
| 2,828,328 | 3/1958 | Schmidt et al. | 260/472 |
| 5,002,953 | 3/1991 | Hindley | 514/275 |

OTHER PUBLICATIONS

Chemical Abstracts vol. 52, 11930–1 (1958).
Jour. Amer. Chemical Soc. 80 4320–3 (1958) "Local Anesthetics" Freifelder et al.
Encyclopedia of Chemical Tech., Kirk–Othmer Third Ed., vol. 19, pp. 521–531 (1982).

*Primary Examiner*—Richard L. Raymond

[57] ABSTRACT

N-benzyl-N-organo-substituted aminoalkanol is prepared by reacting benzyl chloride or substituted benzyl chloride with an organo-substituted aminoalkanol in the presence of a molar excess of the starting aminoalkanol and, optionally, water, and in the absence of a) an organic solvent for the reactants and b) alkali metal hydroxide. A portion of the excess aminoalkanol may be substituted with an alternative amine or dissolved alkali metal carbonate.

14 Claims, No Drawings

PROCESS FOR THE PREPARATION OF N-BENZYL-N-ORGANOAMINOALKANOL

BACKGROUND OF THE INVENTION

This invention is a process for manufacturing N-benzyl, or substituted N-benzyl,-N-organosubstituted aminoalkanol, as further defined herein, having low levels of ether by-product. More particularly, the process comprises reacting benzyl chloride, or substituted benzyl chloride, with an organo-substituted aminoalkanol in the absence of an organic solvent and alkali metal hydroxide to provide a product which does not require distillation.

Certain of the products of the process of this invention have been reported to be useful in preparing local anesthetics.

PRIOR ART

Various N-benzyl-N-organo-substituted aminoalkanols are known. N-benzyl-N-alkylaminoalkanols, wherein the alkyl group contains from 1 to 8 carbon atoms and the alkanol moiety has from 2 to 4 carbons, are disclosed in M. Freifelder et al., (Abbott Labs) J. Amer. Chem. Soc., 80, 4320 (1958). These compounds were prepared using several disclosed procedures. In each, benzaldehyde is reacted with a primary or secondary amine to obtain the tertiary amine. The reactions occur in a solvent for the reactants.

U.S. Pat. No. 5,002,953 discloses the preparations of N-benzoxazolyl-N-isopropylaminoethanol by reacting 2-chlorobenzoxazole with 2-isopropylaminoethanol and triethylamine dissolved in tetrahydrofuran.

Kirk-Othmer's "Encyclopedia of Chemical Technology", Third Edition, Vol. 19, pp. 521-531, discloses that quaternary ammonium compounds are conventionally prepared by the reaction of a tertiary amine with an alkylating agent, including benzyl chloride. Primary and secondary amines are also disclosed as useful for the preparation of quaternary ammonium compounds by reaction with an alkylating agent and a basic material (caustic soda) must be present to neutralize the acidic by-product.

STATEMENT OF THE INVENTION

This invention is a process for the preparation of an N-benzyl-N-organo-substituted aminoalkanol comprising reacting a benzyl chloride of the formula:

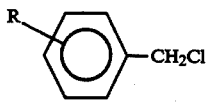

where R is an organic or inorganic group, with at least a stoichiometric amount of an aminoalkanol of the formula:

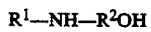

where $R^1$ is a $C_1$–$C_6$ alkyl or aryl group and $R^2$ is a $C_2$–$C_6$ alkylene group, in the absence of a) an organic solvent for the reactants and b) alkali metal hydroxide, and in the presence of sufficient additional hydrochloric acid accepting amine to avoid by-product hydrochloric acid interference with the reaction. Some of the additional amine may be replaced or substituted with the alkali-metal carbonate dissolved in water.

DETAILED DESCRIPTION OF THE INVENTION

The process of this invention relates to the preparation of certain benzyl, or substituted benzyl, organoaminoalkanols without the concurrent formation of ether by-products, and in the absence of organic solvents (other than the amine reactants or hydrogen chloride acceptors).

In an attempt to develop a commercially acceptable process for the preparation of N-benzyl-N-isopropylaminoethanol of pharmaceutical grade, benzyl chloride was reacted with N-isopropylaminoethanol in the presence of caustic soda (25% aqueous solution). The presence of the caustic soda was believed necessary to take-up the by-product hydrochloric acid which would cause the reaction to terminate after production of the initial batch of benzylisopropylaminoethanol. It was found that the presence of caustic soda in the reaction undesirably favors the coproduction of the ether by-product of benzylisopropylaminoethanol. Similarly, it was found that even traces of sodium hydroxide (caustic soda), e.g., as found in recycled excess isopropylaminoethanol from this process, or after treating the aminoethanol hydrochloride by-product with aqueous caustic soda to free the N-isopropylaminoethanol for reuse in the process, led to the formation of the benzyl-ether by-product. To obtain a purified N-benzyl-N-isopropylaminoethanol from a reaction employing caustic soda requires fractional distillation of the crude product under reduced pressure to remove the ether. If the starting aminoethanol is recycled using caustic soda, as mentioned above, then the free or dissolved NaOH must first be neutralized with aqueous hydrochloric acid in order for it to be used in the process disclosed herein to avoid the formation of the benzyl ether by-product.

The presence of a foreign organic solvent for the reactants in the reaction for the preparation of benzylorganoaminoalkanol, as employed in the prior art reaction of benzaldehyde with an alkylaminoethanol, is also considered undesirable for a commercial process since it requires additional steps to separate and recycle the solvent.

As previously explained, the reaction, as employed herein, requires either at least two moles of aminoalkanol reactant for each mole of (substituted) benzyl chloride, or an alternative amine replacement for amounts of the aminoalkanol in excess of stoichiometric (a mole ratio in excess of 1). This additional amine component serves to accept or take up the acid by-product of the reaction, i.e., hydrochloric acid, to form an amine hydrochloride. If the free acid is not taken up or removed, the desired reaction will not proceed after the initial product formation since the starting amine will not be available for reaction as it has been converted to the aminehydrochloride.

The alternative amines used for acceptance of the hydrochloric acid by-product will include certain tertiary (t) amines including t-cycloaliphatic amines and heterocyclic nitrogen compounds, for example, trialkylamines, trialkanolamines, alkylaminodialkanols, N-alkyl piperidine, N,N-dialkyl piperazine and the like. These hydrochloric acid acceptors may be substituted with, e.g., $C_1$–$C_6$ alkyl groups.

Surprisingly, in the practice of the process of this invention, no detectable quaternary amine products are formed. This is unexpected in the light of the literature which discloses that benzyl chloride can react with tertiary amines or aminoalcohols to produce quaternary amine compounds. (See Kirk-Othmer citation, supra).

If desired, the alternative amine or aminoalkanol in excess of stoichiometric, may be replaced, almost completely, with an alkali metal carbonate, which includes bicarbonates, to neutralize the hydrochloric acid by-product.

In addition to the preferred benzyl chloride reactant for the process of this invention, substituted benzyl chlorides wherein the substituent groups are attached directly to the benzyl ring, may be used. The substituents include, e.g, $C_1$-$C_6$ alkyl, nitro, cyano, halo and carboxyester groups.

The organo-substituted aminoalkanol reactant of the process of this invention includes, for example, $C_1$-$C_6$ alkyl and aryl substituted amino $C_2$-$C_6$ alkyl and aryl substituted amino $C_2$-$C_6$ alkanols. The preferred aminoalkanol is N-isopropyl aminoethanol based on the pharmaceutical usefulness of the end product.

The temperature of the reaction will range from about 25° to about 110° C., preferably between about 50° and 100° C. The pressure of the reaction is not critical and is generally ambient or atmospheric.

Reaction times range between about 2 and about 20 hours, preferably between about 3 and 6 hours.

The mole ratio of aminoalkanol to benzyl chloride in the reaction generally ranges from about 1:1 to about 4:1; preferably from 1.1:1 to about 2.2:1. As previously explained, when the aminoalkanol to benzyl chloride ratio is less than 2, sufficient alternative amine or alkali metal carbonate is added to make up the deficiency and to react with the by-product hydrochloric acid to avoid its interference with the reaction. The alkali metal carbonate, preferably sodium carbonate, can be used to replace some of the amine (aminoalkanol or alternative amine) in excess of stoichiometric. The carbonate is dissolved in water and is added to the reaction mix as an aqueous solution or added dry to become dissolved in the water, if already in the reaction mix. The carbonate can be present in the reaction mix in an amount, based on moles of carbonate per mole of amine, of from 0.5:1 to 2:1, preferably 0.5:1 to 1:1.

Water may be present in the reaction process in an amount ranging from 0 to about 50%, based on the weight of the amine component, preferably from about 10 to about 40%. water facilitates stirring of the reaction mix by decreasing its viscosity.

The following examples are set forth to demonstrate the invention.

EXAMPLE 1

To a 500 ml round bottom flask, heated by immersion in an oil bath and equipped with a magnetic stirring bar, thermometer, air condenser and addition funnel (all in a glove box) was added 160.0g of 25% sodium hydroxide solution (1.0 mole) and 241.0 ml (95% assay) of N-isopropylaminoethanol (2.0 moles). The mixture was vigorously stirred and heated to 50° C. Benzyl chloride was added dropwise from an addition funnel until 115.0 ml had been added (1.0 mole). When the addition was completed the temperature of the reaction mixture was raised to 70°-80° C. and the mixture was heated for 3 hours. The gas chromatograph (GC) of the top amine layer indicated that product was formed but with a significant amount of by-product benzyl ether.

In another experiment, starting with less sodium hydroxide, the by-product benzyl ether was still produced (approximately 5% at about 60% product conversion).

This example indicates that carrying out the reaction in the presence of aqueous alkali metal hydroxide leads to significant amounts of by-product benzyl ether.

To obtain the pure product, it is necessary to carry out a fractional distillation under reduced pressure.

EXAMPLE 2

To an apparatus as described in Example 1 was added 241.01 ml (95% assay) N-isopropylaminoethanol (2.0 moles) and this was heated to 55° C. 116.0 ml (1.0 mole) of benzyl chloride was then added dropwise over a 1 hour period. The temperature rose to 60° C. following the addition of benzyl chloride and stayed at 60° C. for about 1 hour. The mixture turned a pink color and became a thick gel. After about another hour, 150 ml water was added and the mixture stirred. Two layers separated. The top product layer weighted 199.0 g (theoretical yield is 193.0 g) and its GC indicated it contained 92.0% product, 4.0% benzyl chloride and no significant amount of the unwanted benzyl ether by-product. The lower aqueous layer weighed 292.8 g.

Heating a vial of a small amount of the top product layer with fresh isopropylaminoethanol to 60°-75° C. produced GC data indicating that the residual benzyl chloride reacts further to product. Repeating this on a larger scale, 199.0 g of top layer and 14.5 ml (0.127 mole) of isopropylaminoethanol were heated at 60°-76° C. for 5 hours to reduce the residual benzyl chloride to 0.4% (GC area %). Further heating, washing with two 100 ml portions of water, and stripping of the residual water in a rotary evaporator gave a product with less than 0.1% residual N-isopropylaminoethanol, no detectable benzyl chloride and about 0.1% of the by-product benzyl ether. The advantage of this procedure over Example 1 is that a significant production of the by-product ether is avoided and fractional distillation under reduced pressure is not required to obtain a product of about 98% purity.

EXAMPLE 3

To an apparatus as described in Example 1 was added 120.5 ml (95% assay) of N-isopropylaminoethanol (1.0 mole) and 14.0 ml of deionized water. The solution was heated to 55° C. and benzyl chloride (58.0 ml or 0.5 mole) was added dropwise over a 2 hour period. A slight exotherm (55°-62° C.) was noticed. The reaction was stirred and heated to 55° C. for about another hour and the heat turned off while stirring continued during the cool down cycle. The next day the reaction mixture was heated from 52°-93° C. (bath temperature), 50°-81° C. (reaction temperature), for another 6 hours (3 hr. at 81° C.) to give complete reaction of the benzyl chloride (GC analysis showed 97-98% product, 1% starting amine and 0.1% benzyl ether by-product). After adding 50 ml of water, the top product layer weighed 90.2 g (93% yield) and the lower layer weighed 127.0 g.

The advantage of the procedure of Example 3 over Example 2 is that the water that is initially present provides a much less viscous solution without affecting the purity of the product. This less viscous solution is much more easily stirred.

EXAMPLE 4

To an apparatus as described in Example 1 was added 72.3 ml (0.6 mole) of (95% assay) N-isopropylaminoethanol, and a solution of 26.5 g (0.25 mole) of sodium carbonate in 60.0 ml of water at 35° C. The mixture was heated to 50° C. while benzyl chloride was added dropwise until 58.0 ml (0.5 mole) had been added. Then the temperature of the oil bath was raised to 90° C. and the reaction mixture heated at 50°–85° C. The next day the reaction mixture was heated at 78°–83° C. for 6.25 hours plus about another hour the following day at 83° C. to give complete reaction of the benzyl chloride. The GC analysis indicated that the product had no significant amount of by-product benzyl ether present.

EXAMPLE 5

To an apparatus as described in Example 1, except that the magnetic stirring bar was replaced with a mechanical stirrer, was added 67.1 g (0.65 mole) of 98.3% assay N-isopropylaminoethanol and a solution of 26.5 g (0.25 mole) of sodium carbonate in 60 ml of water at about 30°–35° C. The mixture was heated to 100° C. and 63.2 g (0.5 mole) of benzyl chloride was added dropwise over 20 minutes. Then, the reaction mixture was heated from about 3 to 4 hours until all the benzyl chloride had reacted as determined by GC analysis. Following completion of the reaction, 50 g of water was added and the mixture stirred to dissolve the salts and to cause the mixture to separate into two layers. The upper (product) layer was separated and weighed 98.3 g and the lower (aqueous) layer weighed 157.5 g. The upper (product) layer was washed with 100 g of water and 96 g of washed product was recovered as an upper layer along with 101 g of an aqueous lower layer. The washed product was analyzed by GC and found to be 97.4% N-benzyl-N-isopropylaminoethanol, 0.64% starting aminoethanol and 0.36% of the benzyl ether by-product.

We claim:

1. A process for the preparation of an N-(substituted) benzyl-N-organo-substituted aminoalkanol comprising reacting a benzyl chloride of the formula:

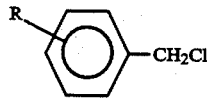

where R is an organic or inorganic group, with at least a stoichiometric amount of an aminoalkanol of the formula:

where $R^1$ is a $C_1$–$C_6$ alkyl or aryl group and $R^2$ is a $C_2$–$C_6$ alkylene group, in the absence of a) an organic solvent for the reactants and b) alkali metal hydroxide, and in the presence of at least sufficient additional hydrochloric acid accepting amine, if needed, to avoid by-product hydrochloride interference with the reaction.

2. The process of claim 1 wherein the benzyl chloride is unsubstituted benzyl chloride.

3. The process of claim 1 wherein the aminoalkanol is a $C_1$–$C_6$ alkylaminoethanol.

4. The process of claim 1 wherein the aminoalkanol is reacted with the benzyl chloride at a mole ratio of at least 2 up to about 4.

5. The process of claim 1 wherein up to 100% of the additional hydrochloric acid accepting amine is replaced with an alkali metal carbonate.

6. A process for the preparation of N-benzyl-N-($C_1$–$C_6$) alkylaminoethanol comprising reacting an N-($C_1$–$C_6$) alkylaminoethanol in a mole ratio of from 1 to 4 with benzyl chloride in the absence of a) an organic solvent for the reactants and b) alkali metal hydroxide, and in the presence of at least sufficient additional hydrochloric acid accepting amine, if needed, to avoid by-product hydrochloride interference with the reaction.

7. The process of claim 6 wherein said mole ratio is from 2 to about 4.

8. The process of claim 6 wherein the reaction is carried out at a temperature of between about 25° and about 100° C. and at atmospheric pressure.

9. The process of claim 6 wherein water is present in the reaction in an amount of from about 10 to about 40%, based on the weight of aminoalkanol.

10. The process of claim 11 wherein up to 100% of the additional hydrochloric acid accepting amine is replaced with an alkali metal carbonate.

11. A process for the preparation of N-benzyl-N-isopropylaminoethanol comprising reacting N-isopropylaminoethanol at a mole ratio of from about 1.1 to about 2.2 with benzyl chloride in the absence of a) an organic solvent for the reactants and b) alkali metal hydroxide, and in the presence of from about 10 to about 40% water, based on the weight of the aminoethanol, and at least sufficient additional hydrochloric acid accepting amine, if needed, to avoid by-product hydrochloride interference with the reaction, and carrying out the reaction at a temperature ranging from about 50° to about 80° C.

12. The process of claim 11 wherein said mole ratio is at least 2.

13. The process of claim 11 wherein said hydrochloric acid accepting amine is triethylamine.

14. The process of claim 11 wherein up to 100% of the additional hydrochloric acid accepting amine is replaced with an alkali metal carbonate.

* * * * *